US005865141A

United States Patent [19]

Poynter et al.

[11] Patent Number: 5,865,141

[45] Date of Patent: Feb. 2, 1999

[54] STABLE AND REPRODUCIBLE SEALED COMPLEX ECOSYSTEMS

[75] Inventors: Jane Poynter, Oracle, Ariz.; Grant A. Anderson, San Jose, Calif.; Taber MacCallum, Oracle, Ariz.

[73] Assignee: Paragon Space Development Corp., Tucson, Ariz.

[21] Appl. No.: 589,654

[22] Filed: Jan. 22, 1996

[51] Int. Cl.[6] .......................... A01K 61/00; A01K 63/00; A01G 9/02; A01B 79/00

[52] U.S. Cl. .......................... 119/246; 119/200; 119/245; 119/247; 47/1.01; 47/58; 47/69; 800/2; 800/200

[58] Field of Search ................................ 47/1.01, 58, 69; 119/200, 245, 246, 247; 800/2, 200

[56] References Cited

U.S. PATENT DOCUMENTS

| | | | |
|---|---|---|---|
| 3,957,017 | 5/1976 | Carmignani | 119/3 |
| 4,093,546 | 6/1978 | Taborsky | 210/150 |
| 4,117,805 | 10/1978 | Ward | 119/5 |
| 4,122,800 | 10/1978 | Mangarell | 119/5 |
| 4,958,953 | 9/1990 | Hurlburt | 119/5 |
| 5,054,424 | 10/1991 | Sy | 119/5 |
| 5,135,400 | 8/1992 | Ramey | 434/297 |
| 5,183,004 | 2/1993 | Trent | 119/5 |
| 5,322,035 | 6/1994 | Hawes | 119/227 |
| 5,328,049 | 7/1994 | Ritzow | 220/345 |

OTHER PUBLICATIONS

C Tamponnet et al (1994) J Biological Education 28:167–174.

*Primary Examiner*—Bruce R. Campell

[57] ABSTRACT

An apparatus and method for establishing a sealed ecological system that is self-sustaining, remains in dynamic equilibrium over successive generations of organisms. The wastes generated by one set of organisms are consumed entirely by other organisms as nutrients. This nutrient-waste balance is achieved by limiting the amounts of carbon, nitrogen, phosphorous and potassium present at the start-up of the system. Further stability and water clarity is achieved by the use of aquatic plants.

10 Claims, 1 Drawing Sheet

14 16 5 26 10 12 28 30 34 32 20

STABLE AND REPRODUCIBLE SEALED COMPLEX ECOSYSTEMS

FIELD OF THE INVENTION

This invention relates to a sealed ecological system that is completely isolated from the earth's environment, yet is self-sustaining. The sealed system is stable and allows reproduction of animals and plants over many generation with no intervention.

BACKGROUND OF THE INVENTION

Sealed systems that contain living organisms and utilize photons as an energy source to maintain the health of living organisms inside usually are called "closed ecological systems". While many simplified closed ecological systems exist, complex systems that remain in dynamic equilibrium over multiple generations of macro organisms exploiting closed-loop gas and nutrient cycles have been desired but were not attained until the present invention.

One advantage of a sealed environment with a complex ecosystem is that biogeochemical processes occurring within the system can be quantified and the genetic make up of the system can be controlled. Scientific study seeks to vary only one parameter at a time. Sealed ecological systems allow for such parameter control. For example, by the control of one parameter among many, the biogeochemical and ecosystem effects of the one variable can be studied. Studies can employ multiple sealed systems to analyze the impact of various parameters. For example, the effects of low level industrial pollution, or the fate of a new genetically-engineered organism in an ecosystem lend themselves to such study.

Previous to the invention described herein, short-term stability was obtained only in simple closed ecosystems that did not include plants and for only as long as the animals contained in the system survived. The animals were not reproducing. The lack of species diversity in these systems as well as the non-reproducing animals make these systems less desirable than the present invention for research purposes. The present invention provides a closed ecological system which remains in dynamic equilibrium, in which material cycles are closed, and which contains species from the kingdoms plantae, animalia or fungi that reproduce and sustain multiple generations.

Previous prior art attempts at creating a stable, complex, closed ecological system have met with limited success and have used the following three principles. First, enhance net primary production by providing a nutrient supply for photosynthetic organism that maintains a high rate of photosynthesis, which ensures adequate food and oxygen for organisms in the system. Second, enhance net primary production by providing a source of carbon for the photosynthetic organisms, maximizing plant production. Third, enhance system stability by providing separate compartments with controlled material exchange between compartments. The inventors of the present invention have found that individually, and in combination, the above three factors used in the prior art actually diminish the stability of a closed ecological system.

Closed ecological systems utilizing the three principles above have been available for years. Systems built by Dr. Claire Folsome of the University of Hawaii starting in the 1960s and the system marketed as the "Ecosphere" are microbially-based, and do not support breeding populations of plants and animals. Although these systems are closed ecosystems, they do not parallel the complex ecosystems found in the natural world. Additionally, because they do not include reproducing populations of plants and animals they are of limited value in research and education. The present invention allows much greater species richness and diversity, and allow all kingdoms of life to exist within a single, relatively small system.

Other ecosystems, designed for aesthetic and educational uses and commonly called vivariums, lack the ability to remain in dynamic equilibrium when sealed for extended periods of time. U.S. Pat. No. 4,122,800 to Mangarell 1978 4,958,593 to Hurlburt et al. 1990 5,328,049 to Ritzow 1994 5,183,004 to Trent et al. 1993 5,054,424 to Sy 1991 5,135,400 to Ramey 1992, and 4,117,805 to Ward 1978, are all variations of the vivarium concept. All of these are meant to be unsealed or never sealed in order to facilitate regular and scheduled cleaning and internal housekeeping of the plants, animal species and soil and/or water changes. Cleaning is necessary because the systems, as assembled, do not contain inherent controls on the proliferation of microbial life forms that will eventually dominate and destroy the life systems within. Thus dynamic equilibrium cannot be maintained in these prior art inventions. For example, Mangarell '800 describes a "self contained" system, but actually contains only the macro organisms, solids or liquid material. Atmospheric gases, particulates, microbial and/or viral life forms are not prevented from entering or exiting the system. These systems are also not transportable. The present invention allows for transportation for display and study.

Biological systems that filter or otherwise cleanse liquid and gas are commonplace. However, most, like U.S. Pat. No. 4,093,546 to Taborsky 1978 or U.S. Pat. No. 3,957,017 to Carmignani et al. 1976, use non-renewable filters to support the biological systems. Thus human intervention is required for maintenance or replacement using such systems. The present invention is self-sustaining and requires no maintenance.

The most ambitious closed ecological system in the prior art is that system known as "Biosphere 2," located in Oracle, Ariz. One patent is applicable to the invention described herein: U.S. Pat. No. 5,322,035 to Hawes et al. 1994, for a Hydrological System for a Closed Ecological System. While the Hawes discloses a hydrological cycle within a closed ecological system, an "ocean", a crabwalk, a desalination process, agricultural systems and particularly mechanical systems are required to maintain stability. Hawes does not provide for the transport of nutrients from one environment to another, with no balancing of nutrient production and uptake between species. Thus, the Hawes system is subject to imbalances which must be controlled by operator intervention. The present invention overcomes the prior art limitations, provides for nutrient transport and balancing without operator intervention. The present invention allows a sealed ecological system to remain in dynamic equilibrium without human intervention.

SUMMARY OF THE INVENTION

The Invention apparatus is a sealed enclosure containing reproducing species of plants and animals that are in dynamic equilibrium. A means of material transport of the nutrients between organisms present in the enclosure is provided. The inclusion of reproducing populations of plant and animals enhances the scientific value of closed ecological systems.

The method of producing this apparatus and similar apparatus is to provide a sealable enclosure and to populate the enclosure with animal and plant species. The reproducing populations of plants and animals is maintained in dynamic equilibrium by restricting one or more macro nutrients and carbon containing compounds available to photosynthetic organisms.

Further objects and advantages are to provide a consistent means of analyzing closed ecological systems that utilize mechanical means in place of one or more of those biological systems described within the specification of this invention. These objects and advantages, as well as further objects and advantages, will become apparent from a consideration of the ensuing description and drawings.

DETAILED DESCRIPTION

Figure 1:
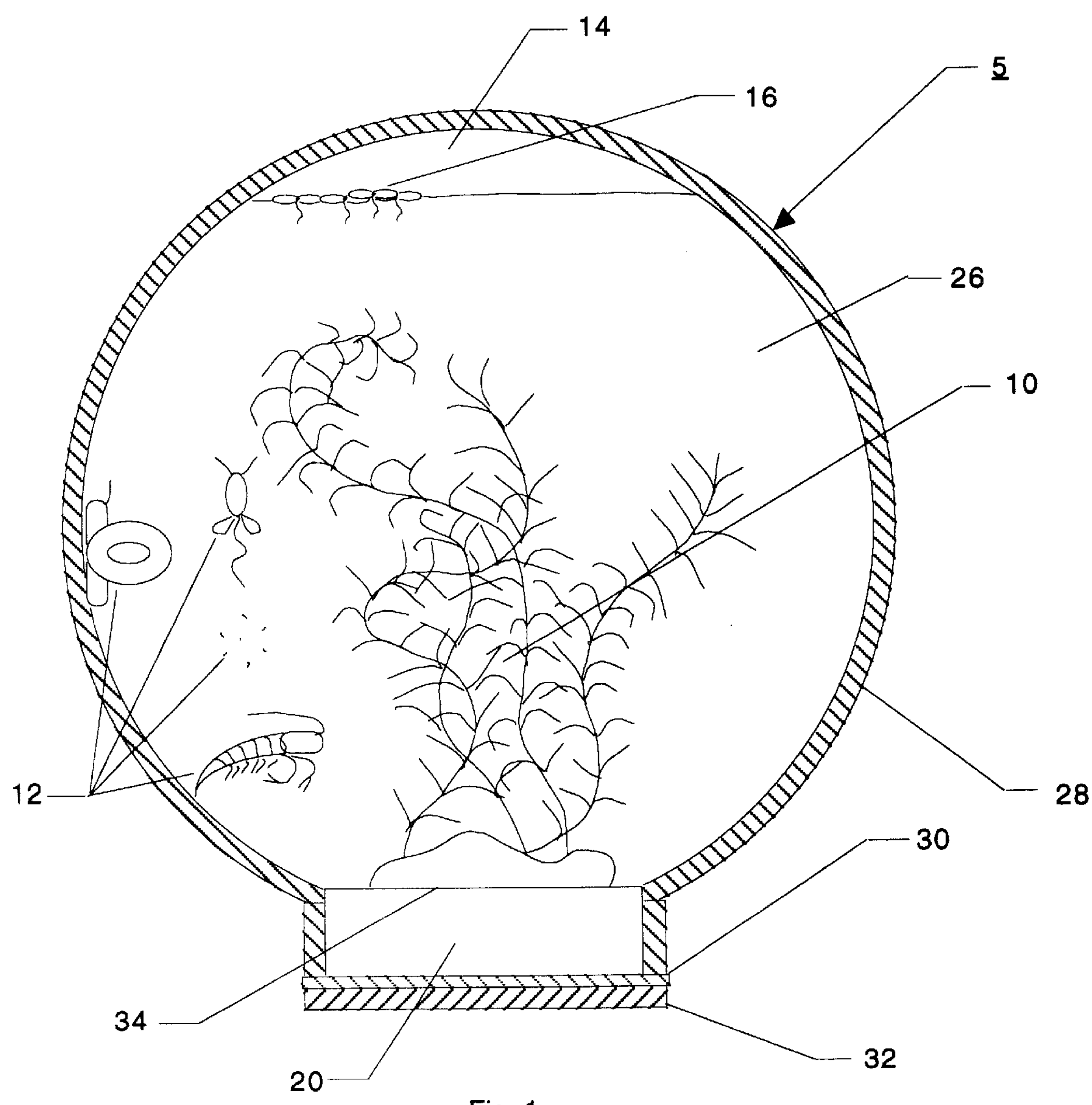
FIG. 1 is a front view of a sealed ecological system containing plants and animals in dynamic equilibrium.

The sealed ecological system may be illustrated by reference to FIG. 1 which shows an embodiment of the present invention. This unit contains reproducing populations of one or more species of organism from each of the kingdoms of plantae and animalia, while also containing a reproducing population from one or more of the kingdoms fungi, protista or monera. The sealed ecological system of the present invention is self-sustaining and remains in dynamic equilibrium over successive generations of inhabitants.

A typical embodiment of the enclosed ecological system is illustrated in FIG. 1. The enclosed ecological system 5, consists of the following items:

A transparent enclosure 28, with an opening 34, in the container through which is introduced the materials contained in the system. The materials are introduced into the system in the following order:

a. A water-based solution 26, consisting of suspended nutrients including potassium, phosphorous, nitrogen and micro-nutrients, such as iron, sufficient to maintain the particular fresh-water life forms. The aquatic animals described in the next section, algal species and microbiota are available commercially and can be bred in ponds in mixed culture 12. A portion of this culture is added to the nutrient solution. The solution provides transportation of nutrients and material through natural convection or external disruption of the system by turning, shaking or otherwise oscillating the system. An air gap 14, of no less than 5% of the total volume is desirable but is not necessary.

b. Detritus from plants and animals 20, containing microbial life forms to break down complex compounds within the detritus into basic compounds and/or nutrients should then be introduced. The detritus forms a layer at the bottom of the vessel once the vessel has been placed on the sealed end after manufacture.

c. Free floating aquatic plants 10, 16, that provide nutrients and oxygen for the animal life are then introduced. The gas composition within the system can be ambient air or other gas composition containing sufficient oxygen to support the animal life. From this time on, adequate lighting must be provided to prevent an excessive accumulation of carbonic acid in the water or carbon dioxide in the air. A sealing structure such as a plastic or glass form 32, and a sealing method such as adhesive or mechanical closures 30, are then placed over the opening to provide an airtight seal preventing material exchange between the outside and inside of the product. The sealing structure 32, or the enclosure itself 28, can contain a airtight but puncturable or openable port, such as a septum, small airlock, or valve, to provide for introduction of foreign substances for the study of the effects of those substances upon the stabilized system. This access port can also be used to draw small samples of the solution, air or organisms for analysis without disturbing the stability of the system. After the sealing compound is cured, or otherwise structurally and materially adequate, the unit can be placed on the sealing disk for display or storage.

Five methods of the present invention, which can be used independently or in combination, produce the desirable characteristic of dynamic equilibrium of the closed ecological system:

1. Material Transport. Material is transported from one organism or set of organisms, to another set of organisms which may include all other organisms within the entire closed ecological system. Such a transportation system may be either active through plumbing, of passive through mixing and diffusion. Exchange of materials between organisms rather than compartmentalizing organisms creates greater long term dynamic equilibrium because populations of organisms grow to carrying capacity and use available resources.
2. Nutrient limitation. By manipulating, controlling or restricting the availability of macro nutrients nitrogen, phosphorous and potassium containing compounds in a system that has adequate material transportation, the need for nutrients in the system by photosynthetic organisms is established before such nutrients are released. When nutrients are then released by heterotrophic organisms such as animals, they are rapidly taken up by photosynthetic organisms in the system. This process of rapid uptake of compounds after they have been released into the system creates stability in the composition of the growth medium which contributes to the stability of the entire system. The manipulation, control or restriction may be accomplished by any means including the use of photosynthetic organisms to remove nutrients from the water. This restriction may also be accomplished by mechanical means, by controlling decomposition, or by simply starting the system with a small amount or available macro nutrients.
3. Carbon Limitation. By manipulating, controlling or restricting the availability of carbon containing compound such as carbon dioxide, in a system that has adequate material transportation, the need for carbon which may be used in the formation of tissues by photosynthetic organisms is established before carbon compounds are released into the system. Then, when carbon compounds are released, for example carbon dioxide released by heterotrophic organisms such as animals through respiration, it can be rapidly utilized by photosynthetic organisms in the system. This process of rapid utilization of carbon compounds after they have been released into a closed system creates stability in the composition of the air and water which contributes to the stability of the entire system. This avoids large swings in carbon dioxide within a system which can create large swings in water pH due to the formation and removal of carbonic acid, resulting in catastrophic collapse of a closed system. The manipulation, control or limitation of carbon compounds may be accomplished by any means including the use of photosynthetic organisms to remove carbon compounds from air and water. This limitation may also be accomplished by either mechanical means, or by controlling decomposition, or simply starting the system with a small amount of available carbon.

4. Aquatic Plants. It has been discovered that when fresh water aquatic plants from several genera are included in the material flow of the closed system, system stability can be enhanced. These genera include but are not limited to Ceratophyllum, Myriophyllum, Limnophila, Bacopa, Cabomba, Ludwigia, Rotala, Cardamine, Lobelia, Hydrocotyle, Mayaca, Utricularia, Fontinalis, Vesicularia, Azolla, Lemna, Limnobium, Pistia, Riccia, Salvinia, Alternanthera, Crassula, Phyllanthus, Egeria, Elodea syn. Anacharis, Lagarosiphon, Wolffia, Sagittaria, Aponogeton, Acorus, Cryptocoryne, Eleocharis, Vallisneria, Nymphaea, Nuphar, Heteranthera, Limnophila and Limosella. This result was not predicted before testing and is believed to be in part because the physiology of these plants is particularly suited to the environment of a closed system and are therefore able to rapidly respond to environmental changes, thereby stabilizing the system. Specifically, when the nutrient transport mechanism is a liquid, aquatic plants are submerged in the transport medium, resulting in intimate contact of the plant with nutrient bearing solutions and the nutrient utilization is rapid. This is consistent with establishing a need for the nutrient to limit the time the nutrient is in solution.

5. Aquatic Animals. Small fresh water aquatic animals from the order Ostracoda and several genera have a stabilizing effect on the system. These genera include Plannaria, Gammarus, Hyalella, Macrocyclops, Daphnia, Helisoma, Physa and Tanichthys. This result was not predicted before testing and is believed to be in part because the physiology and population dynamics of these animals are particularly well suited to the environment of a sealed system, enabling rapid response to environmental changes, thereby stabilizing the system.

The operation of the sealed ecological system after manufacture is dependent on the desire of the person studying the system. However, to maintain a stable, aesthetically-pleasing object, 4 hours or less of sunlight through a closed window and 6–12 hours of indirect light per day is optimal. Alternatively, at least 10 hours of fluorescent light per day is necessary for stability. Darkness for a period of about three days will not harm the system, and the system can recover when placed in the proper lighting. A temperature range of 50° F. to 100° F. with 60°–78° F. is preferred. For scientific study, the access port can be used to introduce foreign substances into the stabilized system, or remove samples for analysis.

As demonstrated in this description, the method, life forms, and materials to create the sealed ecological systems are easily manipulated and combined to created a fully viable sealed ecological system that remains in dynamic equilibrium and is self-sustaining over successive generations of plants and animals. The sealed ecological system is easy and inexpensive to duplicate, allowing for controlled experimentation using multiple sealed ecological systems with controlled variations. The sealed ecological system is aesthetically pleasing and maintenance-free, making it ideal for home or school instruction and entertainment.

Although the description above contains many specifics, these should not be construed as limiting the scope of the invention, but merely provide illustration of the current preferred embodiments of this invention. Other variations will be apparent to skilled persons and should be considered as being within the scope of the present invention.

We claim:

1. A sealed ecological system in which materials are recycled without exchange of materials from outside the system, said system comprising:

an enclosure;

at least one reproducing species from each of the kingdoms of plantae and animalia, excluding humans, within said enclosure;

at least one reproducing species selected from the kingdoms fungi, protista or monera within said enclosure;

means for material transport among species within the system;

wherein photosynthesis is controlled by limiting one or more of the amounts of carbon and macro nutrients necessary for photosynthesis, whereby said system is stable over successive generations as available compounds are used and re-cycled within the system.

2. The system as recited in claim 1 wherein said means for material transport includes water.

3. The system as recited in claim 2 wherein said species of the kingdom plantae are fresh water plants and the species of the animalia are fresh water aquatic animals.

4. The system as recited in claim 3 wherein said fresh water plants are selected from the genera Ceratophyllum, Myriophyllum, Limnophila, Bacopa, Cabomba, Ludwigia, Rotala, Cardamine, Lobelia, Hydrocotyle, Mayaca, Utricularia, Fontinalis, Vesicularia, Azolla, Lemna, Limnobium, Pistia, Riccia, Salvinia, Alternanthera, Crassula, Phyllanthus, Egeria, Elodea, Anacharis, Lagarosiphon or Wolffia, and said fresh water aquatic animals are selected from the orders Amphipoda, Copepoda, Cladocera, Ostracoda or Gastropoda.

5. The system as recited in claim 1 wherein the availability of carbon is no more than 100 mg/kg of organic carbon in water as carbon.

6. The system as recited in claim 1 wherein the availability of nitrogen and phosphorous is no more than 20 ppm in total of nitrite, nitrate and ammonium compounds and no more than 4 ppm phosphate compounds.

7. The system as recited in claim 1 wherein the availability of carbon, nitrogen, and phosphorous is no more than 100 mg/kg of organic carbon in water as carbon, no more than 20 ppm in totality of nitrite, nitrate and ammonium compounds and no more than 4 ppm phosphate compounds in the enclosure.

8. A method of maintaining a sealed ecological system in dynamic equilibrium which comprises:

providing an enclosure containing at least one reproducing species from each of the kingdoms of plantae and animalia, at least one reproducing species selected from the kingdoms fungi, protista or monera, and a means for material transport among the species;

restricting the availability of at least one of carbon, nitrogen, and phosphorous to stabilize the system over successive generations within the system by competition for limited resources;

sealing the enclosure; and exposing the system to light.

9. A method of maintaining a sealed ecological system in dynamic equilibrium as recited in claim 8 wherein said restricting step includes providing no more than 100 mg/kg of organic carbon in water as carbon, no more than 20 ppm in totality of nitrite, nitrate and ammonium compounds and no more than 4 ppm phosphate compounds in the enclosure prior to said sealing step.

10. A kit for facilitating the study of ecological issues, said kit comprising:

at least one reproducing species from each of the kingdoms of plantae and animalia, excluding humans;

at least one reproducing species selected from the kingdoms fungi, protista or monera;

means for material transport among species; and a limited amount of recyclable material selected from the group consisting essentially of organic carbon, nitrogen bearing compounds, potassium bearing compounds, and phosphorous bearing compounds for stabilizing the system as said material is taken up and recycled within the system, whereby said system is stable over successive generations within the system wherein the species, means for material transport, and additive are combined in a suitable enclosure and the enclosure is sealed for study.

* * * * *